United States Patent [19]

Hounsfield et al.

[11] 4,178,511
[45] Dec. 11, 1979

[54] RADIOGRAPHY

[75] Inventors: Godfrey N. Hounsfield, Newark; Richard M. Waltham, London, both of England

[73] Assignee: E M I Limited, Hayes, England

[21] Appl. No.: 934,311

[22] Filed: Aug. 17, 1978

[30] Foreign Application Priority Data

Aug. 18, 1977 [GB] United Kingdom ............... 34679/77

[51] Int. Cl.² ............................................. G03B 41/16
[52] U.S. Cl. .................................. 250/445 T; 250/360
[58] Field of Search ........................... 250/445 T, 360

[56] References Cited

U.S. PATENT DOCUMENTS 4,010,370  3/1977  Le May ........................... 250/445 T

Primary Examiner—Craig E. Church
Attorney, Agent, or Firm—Cooper, Dunham, Clark, Griffin & Moran

[57] ABSTRACT

This application describes a rotation-only CT scanner with beam deflections; the deflection and the rotation being so related as to permit the derivation of absorption data in groups focussed on respective "pivot points" outside the detector locus. Data derived from different detectors, but focussed on the same pivot point, relate to groups of paths, some of which overlap, and the overlap is used to compare the performances of different detectors. To reduce data handling, data provided by adjacent detectors can be combined.

11 Claims, 3 Drawing Figures

RADIOGRAPHY

The present invention relates to radiography, and it relates especially to a branch of radiography which has now become known as computerised tomography.

Computerised tomography permits the absorption (or transmission) coefficient with respect to penetrating radiation, such as X-radiation, to be accurately evaluated at each of a number of elementally sized locations distributed over a cross-sectional slice of the body of a patient under examination. U.S. Pat. No. 3,778,614 describes and claims apparatus for, and methods of, performing computerised tomography.

In principle, computerised tomographic apparatus comprises data acquisition components (commonly referred to as a scanning unit) and data processing components. The data to be acquired and processed relate to the absorption suffered by X-radiation on traversing each of a large number of substantially linear beam paths passing through the desired cross-sectional slice of the patient's body and the reliable acquisition of such data typically takes, at present, twenty seconds (BMI-Scanner computerised tomography system Model CT 5005). The operation of the scanning unit of said system is described in U.S. Pat. No. 3,946,234 and its processing arrangement is described in U.S. Pat. No. 3,924,129.

The success and effectivenss of computerised tomographic systems such as the aforementioned CT 5005 has encouraged a good deal of effort to be expended on finding ways of speeding up the operation of the scanning unit, with the object of producing representations of even greater clarity than those available from systems such as the CT 5005. Other objects of speeding up the operating of the scanning unit are to increase the throughput of patients and to enable the heart to be examined in detail without so great a risk that its motion will blur the representation.

One approach which enables considerably reduction in the acquisition time required by the scanning unit is described and claimed in U.S. patent application Ser. No. 733,941 the specification of which is incorporated herein by reference. This invention is related to the aforementioned earlier application and has, for one of its objects, the aim of selecting a particular class of the considerably range of apparatuses encompassed by the earlier application, which class exhibits certain advantages which will become clear hereinafter.

In order that the invention may be clearly understood and readily carried into effect, one embodiment thereof will now be described, by way of example only, with reference to the accompanying drawings of which:

Figure 1:
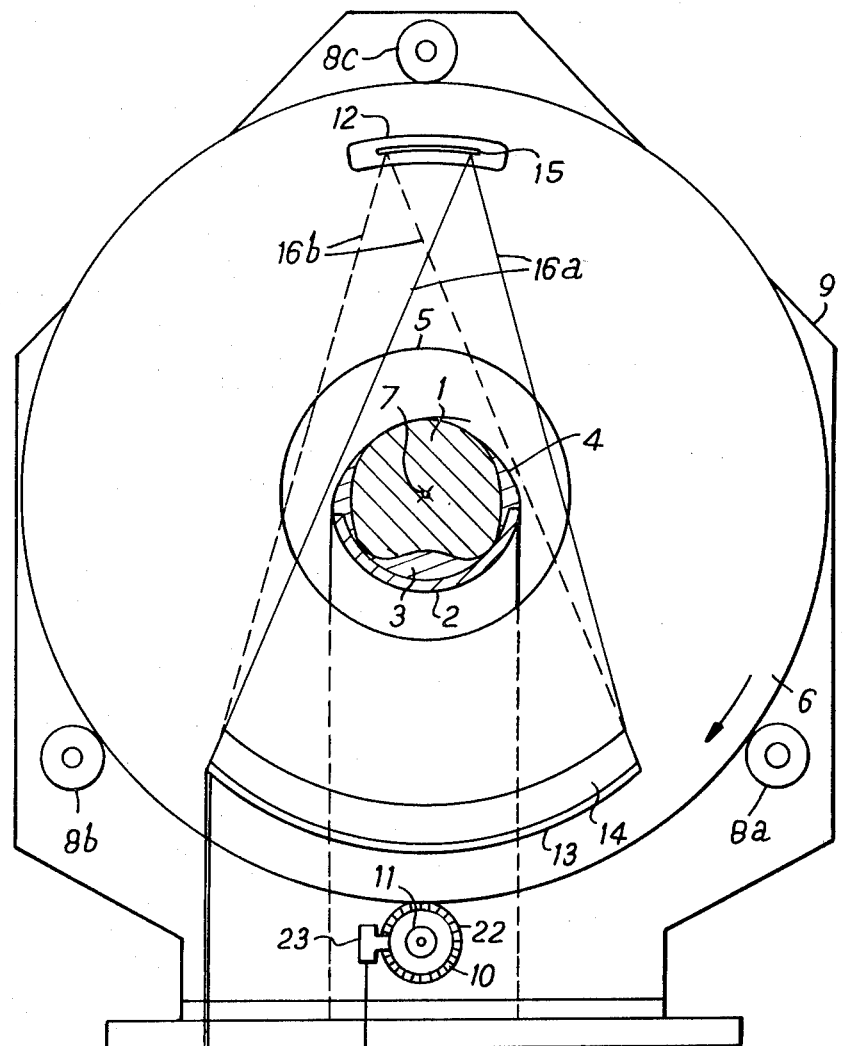
FIG. 1 shows, in front elevational view, an apparatus in accordance with one example of the invention.
Figure 1:
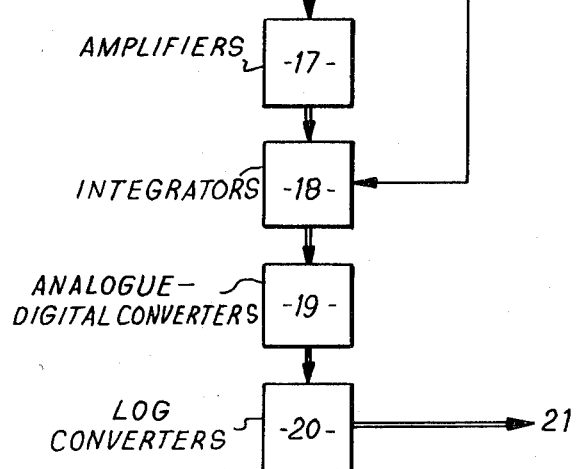

Referring to FIG. 1, which is similar to the corresponding figure of said U.S. application Ser. No. 733,941 there is shown, in front elevation, apparatus in accordance with one example of the invention. A body 1 to be examined, shown in transverse section, is supported on a suitably shaped bed 2 also shown in transverse section. A material 3, having an absorption to the radiation similar to that of body tissue, is positioned between the body 1 and bed 2 to substantially exclude air from the gap therebetween and to provide some support for the patient and is extended partly about the body, to provide an approximately circular cross-section to the radiation. The material 3 may be water or a viscous or particulate material in one or more flexible bags. The body is retained firmly in the desired position by means such as a retaining strap 4.

The bed 2 and the body 1 are inserted into an opening 5 in a rotatable member 6 so that a desired part of the body is centred in the opening. The rotatable member 6 is arranged to rotate about an axis 7, longitudinal of the body and perpendicular to the paper, intersecting the opening 5. For that purpose it is shown schematically as being supported by three gear wheels 8, a.b.c. which engage with gear teeth, not shown, cut into the periphery of member 6. The gear wheels 8 are journalled in a main frame 9 of the apparatus, which may take any form suitable to support the apparatus and to allow the necessary rotation. A further gear wheel 10 also engaging with the said gear teeth, is driven by an electric motor 11, also mounted on the main frame 9, and serves to provide the required rotary motion. The arrangement including the gear wheels 8 is shown for simplicity and clarity, but in practice a large diameter ball race is used. The rotatable member 6 is then formed with a rearwardly projecting flange which is driven by a toothed belt from an electric motor.

The rotatable member 6 also carries a source 12 of x-rays, a bank of detectors 13 and associated collimators 14. The detectors, which in a typical embodiment number 312, can be of any suitable type, for example scintillation crystals with associated optical-electrical signal converters such as photomultipliers or photodiodes.

The source 12 includes an elongated target/anode 15, which will be discussed further hereinafter, and provides a fan-shaped beam 16 of X-rays from origin which can be repetitively scanned, by electronic means, from the position 16a to the position 16b shown. In this example the fan of X-rays extends over 50° and the scan of the origin of the X-rays along target 15 is of the order of 5 cm although it may be more or less than this if desired. The collimators have longitudinal axes which intersect at the centre of the anode 15. The detectors are arranged to intercept the radiation of fan 16 for any position of the origin of the X-rays in its lateral scan along target 15. It should be understood that collimators 14 are of dimensions which allow such interception while preventing the receiption of scattered radiation to the greatest degree practically possible.

In this example, the X-ray source 12 is placed of the order of 50 cm from the central axis 7 with the detectors 13 being placed a further 50 cm on the opposite side of axis 7. If desired, however, the distances from source to axis 7 and detectors to axis 7 may be unequal, without departing from the principles of the invention, provided the geometry of the arrangement is accurately known.

Disregarding for the moment the rotary motion referred to hereinbefore, the arrangement is such that, repetitively, the point of origin of the X-rays is scanned steadily along target 15 taking the fan of X-rays from 16a to 16b, and is rapidly returned to the starting point before repeating the scan. During each such steady scanning movement, each detector of array 13 provides output signals indicative of the intensity of radiation incident thereon in sequence along a number of substantially linear beam paths. These output signals are amplified in amplifiers 17 and then applied to a respective one of a group of integrators 18, one integrator being provided for each detector. Each output signal is then integrated over a period chosen so that it provides an analogue signal representing the total intensity of radiation incident on the respective detector during that time and transmitted through the body 1 along a path effectively examined by that detector taking into account the rotational motion. In this example, the timing of the integration intervals will be considered to provide sixty periods in the time of one "forward" lateral scan of X-ray fan 16 (from 16a to 16b). It will be understood that in practice a larger or smaller number of integration intervals could be provided for each forward lateral scan depending upon the circumstances prevailing. The arrangement of this example ensures therefore that each detector measures radiation, in effect, along sixty narrow beam paths joining that detector with sixty equally spaced positions along target 15. The paths are, of course, of widths determined by the integration intervals and static beam geometry and are of a shape determined by the geometry of scanning movements in those intervals. For the purpose of illustration, however, they may be considered to be represented by single lines which are in fact their centre lines. The lines illustrating the extremes of fan 16 are thus the centre lines of the extreme beams of the fan.

The analogue signals for those paths are then converted to digital form in converters 19 and to logarithmic form in converters 20 for application to further processing circuits 21. It will be understood that one amplifier 17, integrater 18, A/D convertor 19 and log converter 20 is provided for every detector, all operated in synchronism. All of the circuits 15 to 19 are of well known construction. The processing circuits 21 are effective to sort the signals into sets representing absorption along groups of paths having a common characteristic, as will be described in more detail hereafter, for processing by suitable circuits, such as those described in U.S. Pat. No. 3,924,129 to provide the desired representation. If the characteristic of the groups of paths is not parallelism, the technique described in British patent application No. 29,256/77 may be used to compensate for slight errors which would otherwise be introduced into the representation due to the fact that the circuits of U.S. Pat. No. 3,924,129 operate most conveniently upon groups of output signals relating to parallel beam paths.

In order to achieve the effect of the present invention, which will be described in detail hereinafter, the motor 11 provides a continuous clockwise motion of rotatable member 6 and all the equipment mounted thereon, about axis 7 and therefore about the body 1 of the patient on bed 2. The motion of member 6 and the electronic scanning of X-ray fan 16 must be in strict relationship to achieve the desired result. For this purpose the shaft of gear wheel 10 is shown to have mounted, co-axially thereon, a circular graticule 22 in the form of a translucent ring carrying engraved lines. The lines can interrupt a light path between a light source and photocell in a unit 23 mounted on frame 9, so that the photocell provides pulses indicative of the rotary movement of member 6. These pulses may be used both to operate the integrators 18 and to control the X-ray source 12 as described hereinafter. In some cases it can be preferable to provide a graticule of large diameter on the member 6 itself and to derive the timing pulses directly therefrom.

It will be apparent that all paths of the radiation do not intercept equal lengths of the body 1, in view of the approximately circular cross-section of the body and any surrounding material. For this reason the outer detectors of the array tend to give higher outputs than centrally disposed detectors, even for a body of uniform absorption. This effect may be reduced by providing suitably shaped attenuating bodies, not shown, between source 15 and body 1 and/or between body 1 and detectors 13 to substantially equalise the absorbing path lengths. Alternatively, the gains of the respective detectors and/or amplifiers may be suitably adjusted. Alternatively, or in addition, correction factors may be measured in the presence of an artificial body of uniform absorption such as water in a suitably shaped box or a phantom of plastic material. Such correction factors may later be subtracted from the measured output signals for the body 1.

Figure 2:
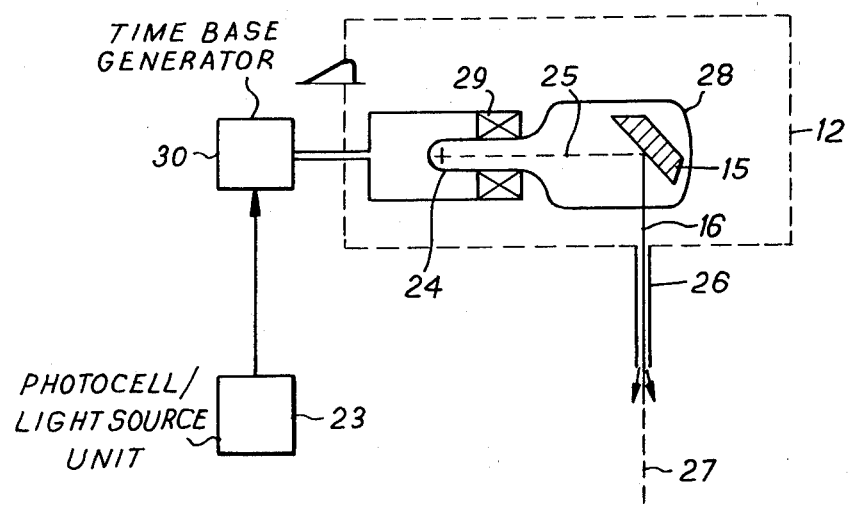
FIG. 2 illustrates an X-ray source suitable for use with the apparatus shown in FIG. 1.

The X-ray source 12 is shown in greater detail in FIG. 2 and comprises an electron gun 24, powered by conventional supply not shown, providing a beam of electron 25 which is incident on target/anode 15 to provide X-ray fan 16. In FIG. 2 the elongation of target 15 is perpendicular to the paper so that the X-ray fan 16 is also perpendicular to the paper. Source collimator 26 is provided, as shown, to restrict the X-rays substantially to the plane of the fan, shown dotted at 27 and that is then the plane of a section of the body 1 to be examined. It will be understood, however, that examination need not be restricted to a plane if this is not desired. The electron gun and target are enclosed in an evacuated envelope 28 having a neck section around which are disposed scanning coils 29 receiving a sawtooth signal from a time base generator 30. In operation the sawtooth voltage from generator 30 scans the point of incidence of the electron beam 25 along target 15 from one end in a direction perpendicular to the paper to scan the X-ray point of origin as shown in FIG. 1. Although a pencil beam of electrons is indicated it will be understood that it may be understood that it may be a ribbon shaped beam used in conjunction with a suitable shape of target 15. Furthermore, oil cooling of target 15, although not shown, is preferably provided in a conventional manner. Although scanning coils have been shown in FIG. 2, deflection plates may be used if desired; any configuration of source 12 capable of achieving the scanning of the X-ray fan 16 being suitable for use with the invention.

As mentioned hereinbefore, time base generator 30 provides the scanning sawtooth voltage in conventional manner and to provide the desired scanning relationship this sawtooth is to be maintained in a correct phase with the rotation. The exact relationship used is determined by the pulses from photocell unit 25. Since the pulses are also supplied to integrators 18, the integration times are retained in the desired relationship with the scanning of X-ray fan 16 to provide the required effective beam paths.

Figure 3:
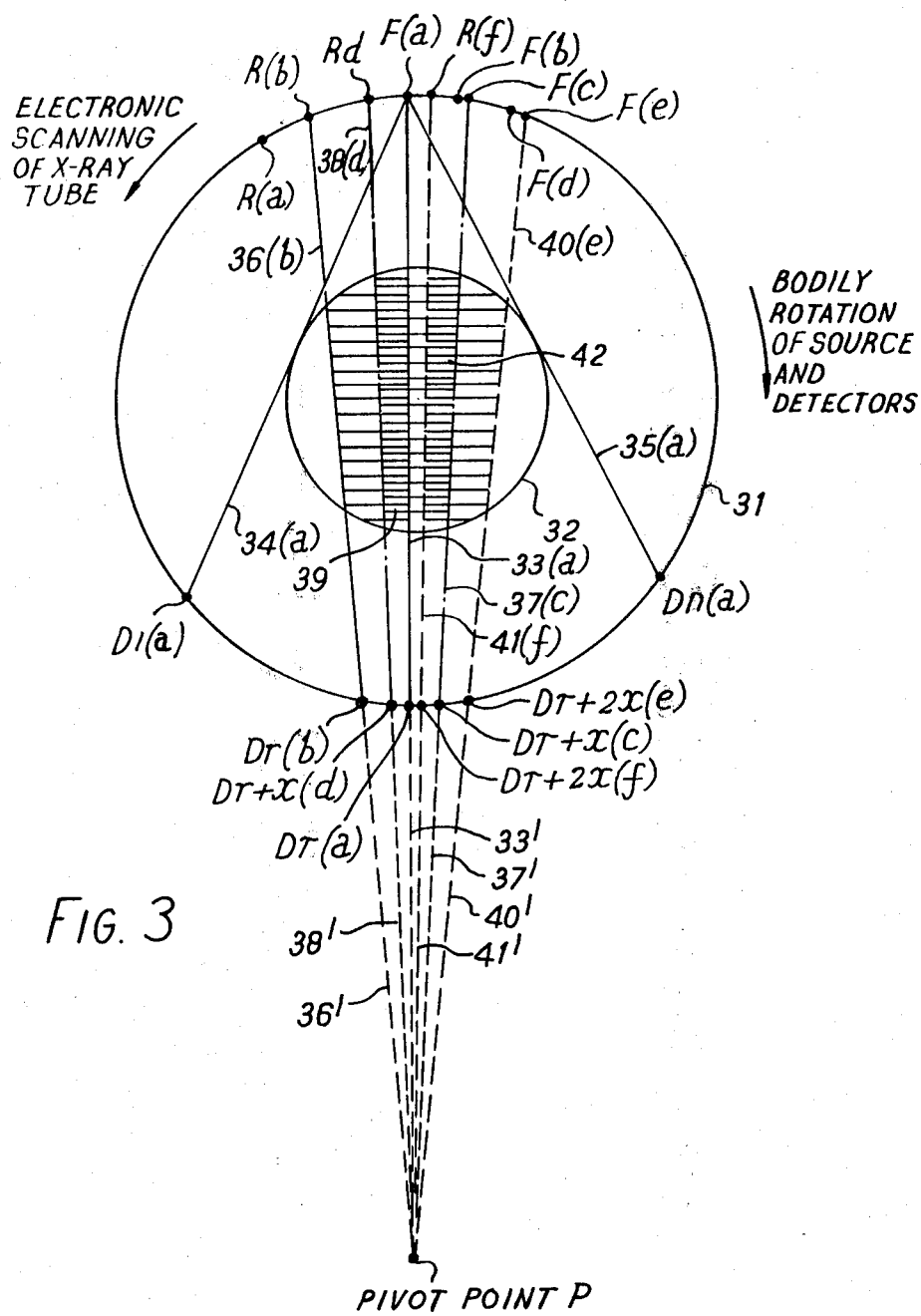
FIG. 3 is a schematic drawing showing the relationship of beam paths for which absorption data are derived in accordance with one example of the invention.

Reference will now additionally be made to FIG. 3 which is explanatory of the operation of an apparatus in accordance with one example of this invention.

In FIG. 3, the outer circle 31 represents the common locus followed by the anode 15 of the X-ray tube 12 and by the detector array 13. The inner circle 32 represents the aperture 5. The positions occupied by the extremities of the anode 15 of the X-ray tube 12 at a number of salient times a to f during an examination are indicated by the reference letters F (front) and R (rear)—with respect to the direction of bodily movement of a member 6—in each case followed by a bracketed lower case letter corresponding to the relevant time, in the range a to f, when the indicated extremity occupies that position. Likewise, the positions of certain of the detectors in array 13 at the aforementioned times as shown; these positions being referenced by the letter D followed by a lower case letter, or lower case letters, indicative of the particular detector concerned and a bracketed lower case letter indicative of the relevant time, in the range a to f, when the identified detector occupies that position.

The first positions to be considered, although it should be noted that these positions do not necessarily constitute positions occupied at the start of an examination, are source front position F(a) and the position Dr(a) occupied by detector Dr at the same time. At that time, (a), the detector Dr receives radiation projected from the front extremity F of the source anode along a beam path 33(a). As previously mentioned, the source anode produces a fan of radiation from whichever region thereof is bombarded by electrons at a given time, and the extremities of this fan, at time (a), are shown at 34(a) and 35(a), falling upon detectors Dl and Dn respectively in positions Dl(a) and Dn(a). It will be appreciated that the detectors Dl and Dn represent the extreme detectors (i.e. the first and last detectors) in the array 13 and that although, for ease of description and clarity of explanation, only a few positions will be specifically described hereinafter, all of the detectors are providing output signals all of the time.

Returning to the beam path 33(a), it will be noted that the path actually stops at the detector position Dr(a), but if this path is extrapolated, as shown by the dotted line 33', it intersects a point P, which is known as a pivot point, the significance of which will be explained later.

While on the source and the detectors are being bodily moved, by the angular motion of member 6, through a given angle θ, moving the front of the target 15 to position F(b) and the detector Dr to position Dr(b), the electron beam of the X-ray tube 12 is swept, as described previously, from the front F to the rear R of the anode 15. The anode has an angular extent of 3θ at the axis 7 of rotation and thus the nett result of the bodily movement of the source in the clockwise direction and the anticlockwise deflection of the electron beam is that, at time (b), the X-rays originate from the position R(b) occupied at the time by the rear of the anode 15. The angle subtended at the central axis 7 by the points F(a) and R(b) is 2θ. The path joining positions R(b) and Dr(b) is shown at 36(b) and if this path is extrapolated, as shown at 36', it will be noted that it intersects the path 33' at the pivot point P. It will thus be appreciated that all of the sixty beam paths from the source to the detector Dr between the times (a) and (b) will, if extrapolated, meet at the pivot point P, at least with a substantial degree of accuracy.

The electron beam of the X-ray tube 12 is next caused to fly back relatively rapidly (as compared with the forward sweep) to the front F of the target. The fly-back, however, cannot be done instantaneously and typically takes about 10% of the forward sweep time. Since the clockwise bodily rotation of the source and detectors is continous, therefore, the next salient position is that indicated at F(c), which is angularly spaced by about θ/10 from the position F(b) which was occupied by the front of the anode at time (b). At time (c), a beam path 37(c), from the position F(c) which, when extrapolated as at 37', passes through the pivot point P, meets the circle 31 at position Dr+x(c), which is the position occupied by detector Dr+x at that time. The letter x represents an integer, and its size will of course be determined by parameters of the system much as the diameter of circle 31, the packing density of detectors in the array 13 and the value of θ.

During the next forward sweep of the electron beam of tube 12 from the front to the rear of the anode 15, the detector Dr+x progresses to the position Dr+x(d). The beam path 38(d), joining the source position R(d) to the detector position Dr+x(d) at time (d), can be extrapolated as at 38' to meet the point P. It will be noted from the drawing (FIG. 3) that the area, within circle 32, which is bounded by the paths 33(a) and 36(b), representing the beam paths followed by radiation falling on detector Dr during the time (a) to (b), overlaps to a considerable extent the corresponding area bonded by the beam paths 37(c) and 38(d) and representing beam paths followed by radiation detected by detector Dr+x during the time (c) to (d). The region of overlap is shown by the double shaded area 39 between the paths 33(a) and 38(d).

The angle subtended at the pivot point P by the paths 33(a) and 38(d) is somewhat less than half of the angle subtended at that point by the paths 33(a) and 36(b) or by the paths 37(c) and 38(d), due to the finite time taken for the aforementioned fly-back to occur. This being the case, and recalling that there are, in this example, sixty beam paths between 33(a) and 36(b) and between 37(c) and 38(d), it will be appreciated that the overlap region 39 contains a little less than thirty beam paths. Typically it contains twenty-seven beam paths.

The fact that the beam paths in the region 39 have been examined by two different detectors (Dr and Dr+x) enables the sensitivity, or other response characteristics, of the two detectors to be compared. This is important matter in multi-detector CT scanners of the kind described here. One way in which the comparison can be done is to sum the output signals derived from detector DR (or their logarithms) for all of the twenty-seven paths in region 39, to form a similar sum for the detector Dr+x and then to compare the two sums. Alternatively, of course, the output signals derived from the two detectors for each individual beam path in region 39, or their logarithms, can be compared and an average taken of the discrepancies. It is important that detector performances are compared, as they are here, on the basis of output signals relating to beam paths distributed over an appreciable area, as opposed to single overlapping beam paths, because the latter technique puts unacceptably high constraints on the accuracy of beam path positioning.

Returning now to FIG. 3, it will be appreciated that the procedure repeats, with the electron beam being caused to fly back from the rear of anode 15 to the front thereof, causing the radiation to originate from position F(e) at time (e). The beam path 40(e) from position F(e) which, when extrapolated as at 40', meets the pivot point P, cuts the circle 31 at position Dr+2x(e). Clearly, radiation projected along path 40(e) will be detected by detector Dr+2x. The subsequent forward sweep of the electron beam of tube 12 takes the source of radiation to position R(f) at time (f) and a beam path 41(f) joining that source position to the position Dr+2x(f) occupied by detector Dr+2x at that time can be extrapolated as at 41' to meet the pivot point P. It will be observed that the beam paths 37(c) and 41(f) bound an area 42, like the area 39, which in this case enables the performance of detector Dr+x has already been compared with that of detector Dr, it can be seen that the three detectors can be normalised in performance.

While this has been going on, i.e. during the periods (a) to (b), (c) to (d) and (e) to (f), other detectors have been examining radiation projected thereto along other beam paths which meet at other pivot points, and comparisons between the performances of various of these detectors are made. Likewise, the procedure continues after time (f) and, associated with each pivot point such as P, are a number of detector comparison zones, such as 39 and 42, distributed across the circle 32, which enable the performances of a group of detectors to be normalised Typically each group includes about twenty-six detectors, there being a total of 312 detectors in the array 13, in this example.

One problem associated with the procedure described hereinbefore is that a considerable amount of data storage is called for. This can be accommodated if desired, but it is preferable to reduce the data to be stored. This can be done by combining the readings taken by a number of adjacent detectors (typically three) at slightly different times so that each combined signal relates to three virtually superimposed beam paths. It is preferable for the superimposed beam paths to overlie one another accurately in the region of the centre of the circle 32 and for them to diverge slightly adjacent the edges of that circle so that the composite beam path, to which the combined signal relates is slightly waisted adjacent the centre of the circle 32. In this example, detectors 1, 2 and 3 are used to produce composite beams, as are detectors 4, 5 and 6; detectors 7, 8 and 9 and detectors 10, 11 and 12. In this example also, the value of x has been taken as 12 and thus the detector group 1, 2, 3 is normalised, by the technique described hereinbefore, with detector groups 13, 14, 15; 25, 26, 27; 37, 38, 39 etc. Likewise, detector group 4, 5, 6 is normalised with detector groups 16, 17, 18; 28, 29, 30; 40, 41 42 etc. and so on. Thus there are four chains of comparisons to be carried out and each chain has associated therewith a respective group of pivot points such as P.

It has previously been mentioned that the output signals (as normalised) are preferably assembled into sets relating to particular groups of beam paths, having a desired characteristic, prior to being processed. In this example it is desired to assemble the output signals into sets relating to groups of paths which have a common pivot point such as P. These pivot point based beam paths are divergent but, because the pivot points such as P are quite remote from the circle 31, they are not so divergent as to produce unacceptable errors in the desired representation if the convolution form of processing as described in U.S. Pat. No. 3,924,129 is employed; particularly if rotation is effected through 360° and the correcting technique described in British Patent Application No. 29,256/77 is utilised.

These pivot point based groups of paths are investigated, as has been explained, by a group of detectors each of which sweeps relative to the body. The individual detector sweeps overlap and thus the detectors can be calibrated for sensitivity. In the example described there are four "strings" of calibration and there are not comparisons between the detectors of different strings. If the output signals had been assembled into sets relating to groups of beam paths originating from a common source position, each group would contain contributions from different detector strings for which no cross-calibration was available.

It is advantageous, and reduces the X-ray dosage to the patient, if the X-ray emission from the tube 12 is suppressed during the electron beam fly-back periods. This also permits the zero level of the detectors to be evaluated. If the modulation is made such that the X-radiation does not stop and start abruptly but instead decays and rises fairly gradually, advantages are obtained in permitting merging of the data obtained with the source adjacent the extremities of the anode 15.

One important advantage of arrangements such as that described hereinbefore is that the source and detectors can be operated at the same distance from the axis 7 of rotation and yet still produce data having sufficient overlap to permit reliable normalisation of detector performances to be effected. Having the source and the detectors so disposed permits the size of the scanner and the fan angle of radiation derived from the source to be optimised.

The advantages of this invention can be realised with pivot points such as P distant d and 2d from the axis 7, where d is the diameter of circle 31. In the event that the source and the detector array are not disposed on the same circle, then d should be considered as denoting the diameter of the circular path followed by the detectors. With suitable arrangement of beam deflection in relation to the bodily rotation of member 6, the pivot points can be disposed behind the source rather than behind the detectors, although the aforementioned range of pivot point positions still applies.

In the event that the gaps, such as 43, produced between overlap regions such as 39 and 42, cannot be suitably filled or otherwise intolerable, the rate of the electron beam deflection can be increased to an extent sufficient to close the gaps. In the example described, an increase of 10% in the deflection rate relative to the bodily rotation rate achieves this end.

What we claim is:

1. Radiographic apparatus including a source of penetrating X-radiation arranged to irradiate a patient position with a flat fan-shaped distribution of the radiation, detector means arranged to receive radiation emergent from the patient position, the detector means including a plurality of detector devices responsive to said x-radiation and extending across the said distribution, scanning means for causing the source and the detector means to move angularly around the patient position about an axis intersecting said position and extending substantially perpendicularly to the distribution of radiation, and further scanning means, synchronised in operation with the first-mentioned scanning means, to move the origin of said distribution of x-radiation, relative to the detector means, angularly in a sense opposite to that of the angular movement caused by said first-mentioned scanning means, the angular movement caused by said further scanning means being repetitive and at a rate higher than that caused by said first-mentioned scanning means; the synchronisation between the operations of the first-mentioned scanning means and the further scanning means causing a detector, during one cycle of the repetitive movement caused by said further scanning means, to provide output signals relating the a group of mutually inclined beam paths traversing said patient position, the group of paths for that detector intersecting, when extrapolated, at a pivot point disposed at a distance from said axis which exceeds the distance of the relevant detectors from said axis.

2. Apparatus according to claim 1 wherein the said synchronisation between the operations of said first-mentioned scanning means and said further scanning means causes, during successive cycles of the repetitive movement caused by said further scanning means, different detector devices to produce output signals relating to respective groups of beam paths which transverse said patient position and, when extrapolated, intersect at said pivot point.

3. Apparatus according to claim 2 wherein the groups of beam paths for which output signals are produced during successive ones of said cycles overlap to a substantial extent within the patient position.

4. Apparatus according to claim 3 including means for comparing signals produced by different detectors where overlap occurs.

5. Apparatus according to claim 4 wherein said means for comparing includes means for individually summing all signals produced by said different detectors where said overlap occurs and means for comparing the sums to produce a rationalising signal.

6. Apparatus according to claim 4 wherein said means for comparing includes means for averaging signals produced by different detectors and relating to substantially the same beam path.

7. Apparatus according to claim 4, including means for building up a chain of comparisons between detector devices distributed across substantially the full width of said distribution of radiation based upon output signals produced by said devices and relating to beam paths which, when extrapolated, intersect at a common pivot point.

8. Apparatus according to claim 1 including means for combining output signals produced by different detector devices and relating to beam paths disposed in substantially the same region of said patient position.

9. Apparatus according to claim 8 including means for combining output signals derived from respective groups of n adjacent detector devices prior to further processing.

10. Apparatus according to claim 9 including means for normalising characteristics of each group of n detector devices with a plurality of other groups of n detector devices on the basis of output signals relating to beam paths intersecting, when extrapolated, at a common pivot point, some of the signals produced from each group relating to beam paths which substantially coincide with beam paths for which signals are produced by at least one other of said groups.

11. Apparatus according to claim 10 wherein n takes the value four.

* * * * *

UNITED STATES PATENT AND TRADEMARK OFFICE
CERTIFICATE OF CORRECTION

PATENT NO. : 4,178,511
DATED : December 11, 1979
INVENTOR(S) : GODFREY N. HOUNSFIELD and RICHARD M. WALTHAM It is certified that error appears in the above-identified patent and that said Letters Patent are hereby corrected as shown below:

Column 1, line 23, delete "BMI" and insert -- EMI --.

Column 1, line 46, delete "considerably" and insert -- considerable --.

Column 5, line 61, "continous" should read -- continuous --.

Column 6, line 35, after "is" and before "important" (line 36), insert -- an --.

Column 6, lines 67 and 68, after "performance of" (line 67) and before "detector Dr+x" (line 68), insert -- detectors Dr+x and Dr+2x to be compared. Since the performance of --.

Column 8, line 20, after "distant" and before "d" insert -- between --.

Column 8, line 61 (Claim 1), after "relating" and before "a" delete "the" and insert -- to --.

Signed and Sealed this

First Day of July 1980

[SEAL]

Attest:

SIDNEY A. DIAMOND

Attesting Officer

Commissioner of Patents and Trademarks